United States Patent
Stainsby et al.

(10) Patent No.: US 10,314,523 B2
(45) Date of Patent: Jun. 11, 2019

(54) METHOD, SYSTEM AND APPARATUS FOR IMAGE CAPTURE AND REGISTRATION IN IMAGE-GUIDED SURGERY

(71) Applicants: Jeff Alan Stainsby, Toronto (CA); Gal Sela, Toronto (CA)

(72) Inventors: Jeff Alan Stainsby, Toronto (CA); Gal Sela, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/513,256

(22) PCT Filed: Nov. 14, 2014

(86) PCT No.: PCT/CA2014/000819
§ 371 (c)(1),
(2) Date: Mar. 22, 2017

(87) PCT Pub. No.: WO2016/074059
PCT Pub. Date: May 19, 2016

(65) Prior Publication Data
US 2017/0258375 A1    Sep. 14, 2017

(51) Int. Cl.
*A61B 5/11* (2006.01)
*A61B 5/055* (2006.01)
(Continued)

(52) U.S. Cl.
CPC ............ *A61B 5/1127* (2013.01); *A61B 5/055* (2013.01); *A61B 34/20* (2016.02); *G01R 33/543* (2013.01);
(Continued)

(58) Field of Classification Search
CPC .. G01R 33/543; G01R 33/5608; G01R 33/58; G06T 2207/10088; G06T 7/0012;
(Continued)

(56) References Cited

U.S. PATENT DOCUMENTS 6,016,439 A * 1/2000 Acker .................. A61B 5/06
600/411
6,044,308 A    3/2000 Huissoon
(Continued)

OTHER PUBLICATIONS

International Preliminary Report on Patentability dated Feb. 27, 2017 for PCT International Patent Application No. PCT/CA2014/000819.

(Continued)

*Primary Examiner* — Peter Luong
(74) *Attorney, Agent, or Firm* — Perry + Currier Inc.

(57) ABSTRACT

A method, system and apparatus for image capture and registration are described. The method includes: obtaining a position of an imaging device in a tracking system frame of reference; obtaining a position of a patient in the tracking system frame of reference; determining, based on the position of the imaging device and the position of the patient, a transformation for registering an imaging device frame of reference with a patient frame of reference; receiving an instruction to capture an image, the instruction including coordinates identifying a target area in the patient frame of reference; applying the transformation to convert the coordinates to the imaging device frame of reference; and controlling the imaging device to capture an image based on the converted coordinates.

21 Claims, 6 Drawing Sheets

(51) Int. Cl.
    *G01R 33/56*     (2006.01)
    *A61B 34/20*     (2016.01)
    *G01R 33/54*     (2006.01)
    *G01R 33/58*     (2006.01)
    *G01R 33/28*     (2006.01)
    *G06T 7/00*     (2017.01)
    *A61B 90/00*     (2016.01)

(52) U.S. Cl.
CPC ......... *G01R 33/5608* (2013.01); *G01R 33/58* (2013.01); *A61B 2034/2055* (2016.02); *A61B 2034/2065* (2016.02); *A61B 2090/374* (2016.02); *G01R 33/28* (2013.01); *G06T 7/0012* (2013.01); *G06T 2207/10088* (2013.01)

(58) Field of Classification Search
CPC ....... A61B 5/1127; A61B 5/055; A61B 34/20; A61B 2034/2065
See application file for complete search history.

(56) References Cited

U.S. PATENT DOCUMENTS

| | | |
|---|---|---|
| 6,405,072 B1 | 6/2002 | Cosman |
| 6,675,040 B1 | 1/2004 | Cosman |
| 6,973,202 B2 | 12/2005 | Mostafavi |
| 2003/0029464 A1 | 2/2003 | Chen et al. |
| 2005/0107689 A1* | 5/2005 | Sasano ................... A61B 5/055 600/425 |
| 2014/0037174 A1 | 2/2014 | Ernst et al. |

OTHER PUBLICATIONS

International Search Report dated Aug. 10, 2015 for International Patent Application No. PCT.CA2014/000819.
Written Opinion dated Aug. 10, 2015 for International Patent Application No. PCT/CA2014/000819.
Lei Qin et al:, Prospective Head-Movement Correction for High-Resolution MRI Using an In-Bore Optical Tracking System. Published Jun. 12, 2009.

* cited by examiner

METHOD, SYSTEM AND APPARATUS FOR IMAGE CAPTURE AND REGISTRATION IN IMAGE-GUIDED SURGERY

FIELD

The specification relates generally to image-guided surgery, and specifically to a method, system and apparatus for image capture and registration in image-guided surgery.

BACKGROUND

Magnetic Resonance Imaging (MRI) is a widely used imaging technology in the medical field. In general, acquiring MRI scans of a patient involves first acquiring one or more preliminary images, referred to as "scout" images. Such scout images are used as a spatial reference from which subsequent targeted MRI scans may be acquired. In other words, the scout images allow the operators of the MRI machine to confirm that the MRI scanner is targeted on the correct portion of the patient before capturing the desired images. The process of acquiring scout images before the desired diagnostic images increases the time required to complete the MRI examination, and by extension increases the cost of the examination as well as the load imposed on the MRI scanner.

Additionally, images acquired using imaging systems such as the above-mentioned MRI scanner may be acquired before a surgical procedure and used during the surgical procedure for guidance. In order to provide effective guidance during the procedure, such images may be aligned (for example, on a display attached to a computer) with images of the patient and surgical instruments .captured during the procedure. Such alignment processes can be time-consuming and inaccurate, and may require pauses in the procedure itself to complete.

SUMMARY

According to an aspect of the specification, a method is provided, including: obtaining a position of an imaging device in a tracking system frame of reference; obtaining a position of a patient in the tracking system frame of reference; determining, based on the position of the imaging device and the position of the patient, a transformation for registering an imaging device frame of reference with a patient frame of reference; receiving an instruction to capture an image, the instruction including coordinates identifying a target area in the patient frame of reference; applying the transformation to convert the coordinates to the imaging device frame of reference; and controlling the imaging device to capture an image based on the converted coordinates.

According to another aspect of the specification, a non-transitory computer readable storage medium is provided, storing a plurality of computer-readable instructions executable by a processor for performing the above method.

According to a further aspect of the specification, a computing device is provided, comprising: an interface; a memory; and a processor interconnected with the interface and the memory. The processor is configured to: obtain a position of an imaging device in a tracking system frame of reference; obtain a position of a patient in the tracking system frame of reference; determine, based on the position of the imaging device and the position of the patient, a transformation for registering an imaging device frame of reference with a patient frame of reference; receive an instruction to capture an image, the instruction including coordinates identifying a target area in the patient frame of reference; apply the transformation to convert the coordinates to the imaging device frame of reference; and control the imaging device to capture an image based on the converted coordinates.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
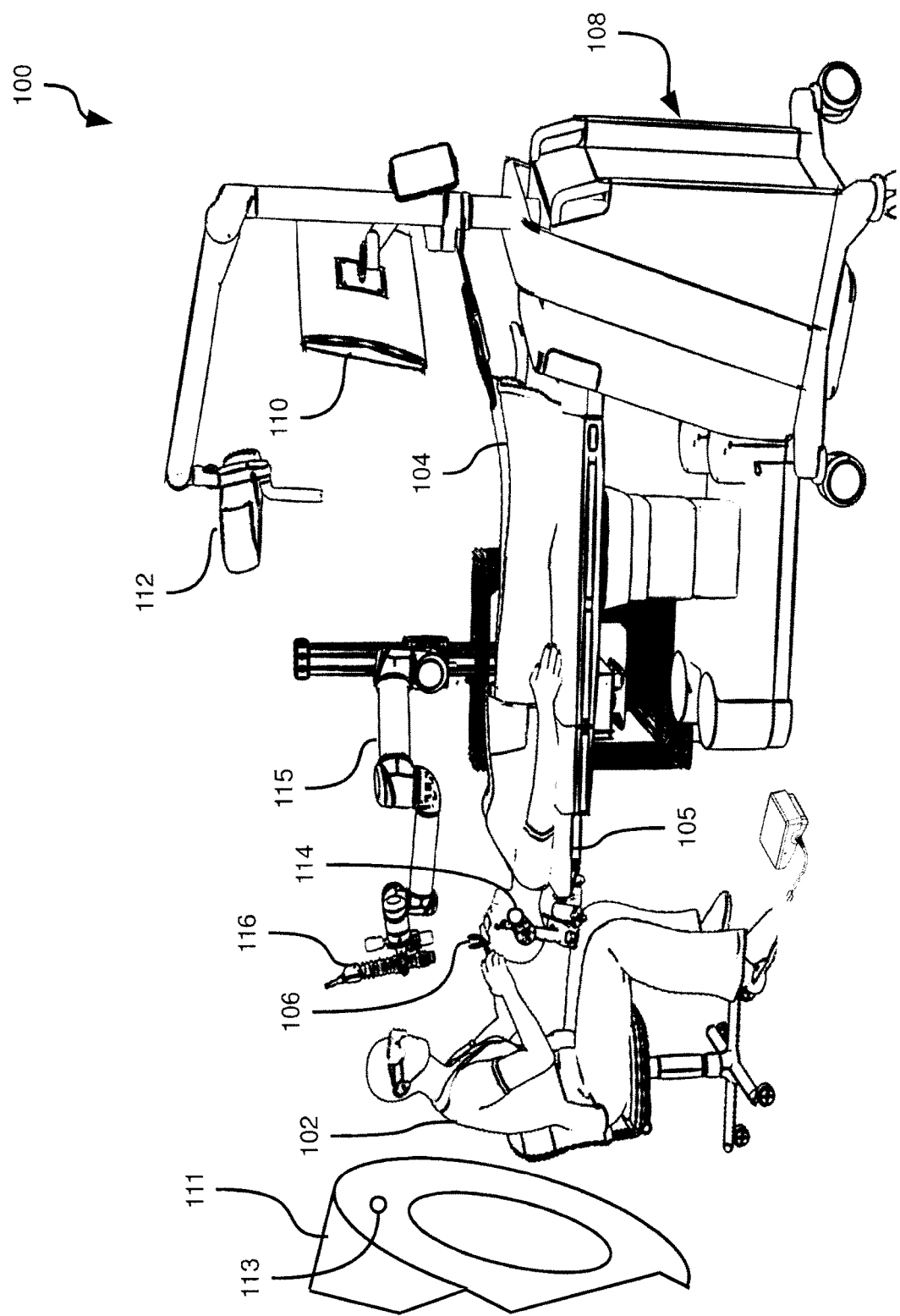
FIG. 1 depicts an operating theatre, according to a non-limiting embodiment.

FIG. 1 depicts a surgical operating theatre 100 in which a healthcare worker 102 (e.g. a surgeon) operates on a patient 104 lying on a bed 105. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. Surgical procedures other than brain surgery may also be performed in operating theatre 100 and make use of the systems and methods described herein.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device. The images provided to display 110 from the computing device can include images captured by an imaging machine 111, which in the present embodiment is an MRI scanner (only partially visible in FIG. 1). A variety of other imaging machines are also contemplated. MRI scanner 111 may be employed to capture images of patient 104 both before and during the medical procedure. To capture such images, bed 105 carrying patient 104 may be moved from its illustrated position into proximity with MRI scanner 111 (for example, to place the head of patient 104 within the bore of MRI scanner 111). In other embodiments, MRI scanner 111 itself may be moveable.

Equipment tower 108 also supports a tracking system 112. Tracking system 112 is generally configured to track the positions of one or more reflective markers mounted on any of the above-mentioned equipment. Example markers 113 and 114 are shown on MRI scanner 111 and patient 104 (specifically, on a bracket fixing patient 104's head to bed 105) respectively. MRI scanner 111 and patient 104 may carry more than one marker in some embodiments. Markers 113 and 114 are also referred to as fiducial markers. Tracking system 112 can include a camera (e.g. a stereo camera) and a computing device (either the same device as mentioned above or a separate device) configured to locate the fiducial markers in the images captured by the camera, and determine the spatial positions of markers 113 and 114 within the operating theatre. The spatial positions may be provided by tracking system 112 to the computing device in equipment tower 108 for subsequent use. Of particular note, the positions of markers 113 and 114 allow for the accurate determination of the positions and orientations of MRI scanner 111 and patient 104, respectively, because MRI scanner 111 and patient 104 have known geometries and markers 113 and 114 are affixed at known locations within those geometries.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object—only one marker is shown on each of MRI scanner 111 and patient 104 for simplicity of illustration. The predefined locations, as well as the geometry of each tracked object, are configured within tracking system 112, and thus tracking system 112 is configured to capture images of operating theatre 100, compare the positions of any visible markers to the preconfigured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 115, also referred to as a robotic arm, carrying an external scope 116 (i.e. external to patient 104). External scope 116 may be positioned over access port 106 by robotic arm 115, and may capture images of the brain of patient 104 for presentation on display 110. The movement of robotic arm 115 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images of patient 104 may be captured using MRI scanner 111. In order to capture such images, instructions may be provided to MRI scanner 111 specifying the location within the scanner at which to capture the images (in other words, targeting MRI scanner 111). During the procedure, additional images of patient 104 may be collected using MRI scanner 111 in a manner similar to that described above. The targeting of MRI scanner 111 is generally based on a target location within patient 104 of which an image is desired. In addition, preoperative and intraoperative images can be presented together on display 110, and either or both of the preoperative and intraoperative images can be presented on display 110 simultaneously with other image data, such as a real-time optical feed from external scope 116.

Figure 2:
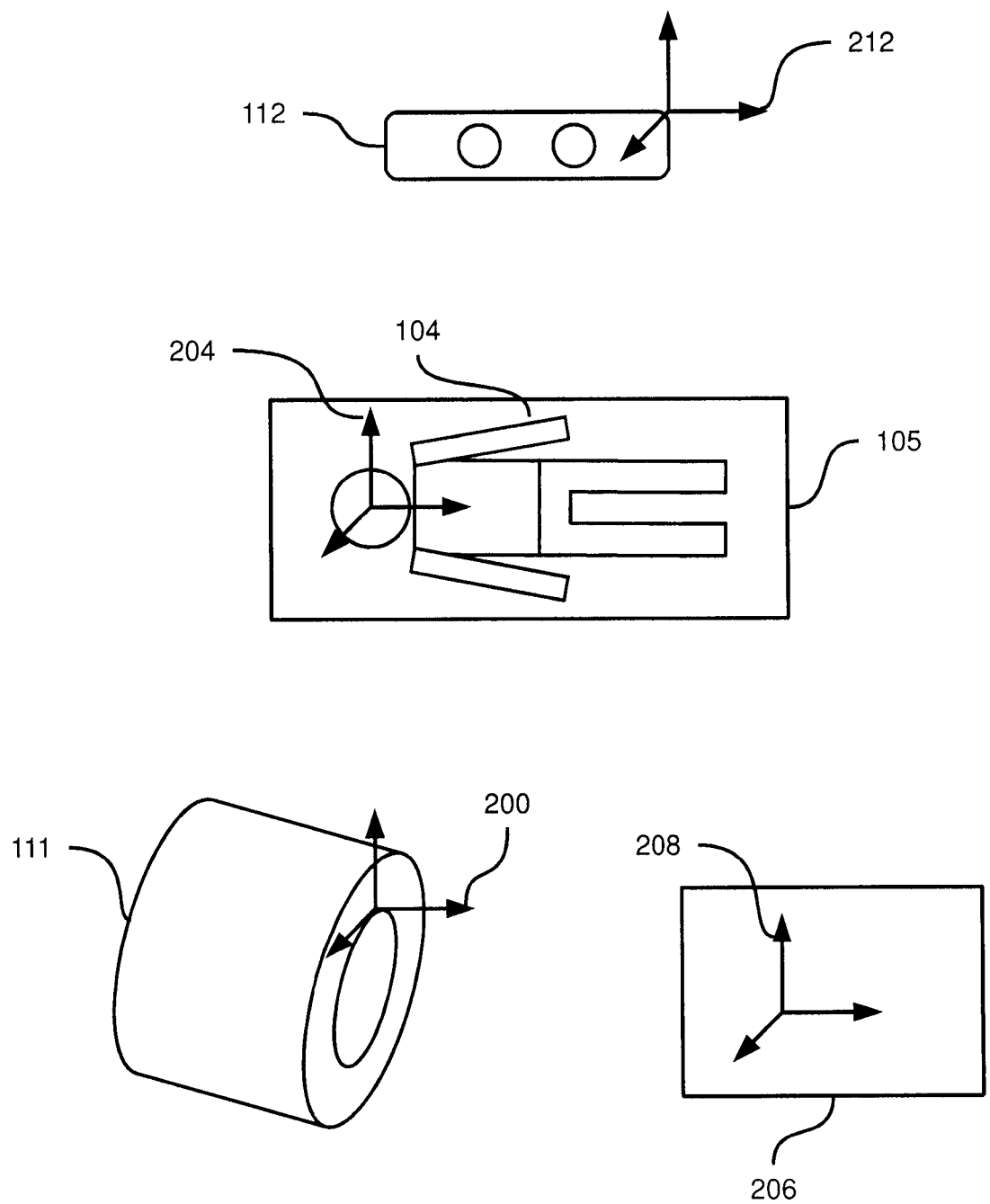
FIG. 2 depicts various frames of reference at use in the operating theatre of FIG. 1, according to a non-limiting embodiment.

As will now be apparent to those skilled in the art, the acquisition of images using MRI scanner 111, and the presentation of various images on display 110 may involve the use of multiple frames of reference. Turning to FIG. 2, examples of such frames of reference will be discussed.

FIG. 2 illustrates MRI scanner 111 and a corresponding frame of reference 200. Frame of reference 200 establishes a coordinate system having an origin at a known location within MRI scanner 111. Instructions to MRI scanner 111, such as instructions to capture an image, generally identify a location within MRI scanner 111 in frame of reference 200. That is, an instruction to MRI scanner 111 may identify a location that is at a specified distance along each of three axes from the origin of frame of reference 200. The origin may be the isocentre of the magnet in MRI scanner 111, or any other predefined location within MRI scanner 111.

Instructions to MRI scanner 111 to capture an image, however, generally originate in a different frame of reference than frame of reference 200. In particular, such instructions generally originate in a frame of reference 204 corresponding to patient 104. That is, if an image of a certain portion of patient 104 is desired, that portion is originally identified by a specified distance along each of three axes from an origin at a known location on patient 104. The origin may be at a predefined anatomical location, or at the location of marker 114, or any other suitable location on patient 104. The axes may be defined in a variety of ways. Conventionally, the axes are defined by the intersections of the sagittal, coronal and transverse planes. The axes may be referred to, for example, as the Left (intersection of coronal and transverse planes), Posterior (intersection of sagittal and transverse planes) and Superior (intersection of sagittal and coronal planes) axes (LPS).

As will now be apparent to those skilled in the art, the targeted portion of patient 104 may not be readily understood by MRI scanner 111. For example, a portion of patient 104 lying at the LPS coordinates (105 mm, 8 mm, 12 mm) relative to marker 114 may be targeted for imaging. The above-mentioned coordinates, however, are not directly usable by MRI scanner 111, as they may refer to different positions within MRI scanner 111 depending on the position of patient 104 within MRI scanner 111. Conventional attempts to locate a targeted patient area within frame of reference 200 generally involve the manual manipulation of alignment mechanisms, such as re-positionable lasers, to establish a landmark on patient 104.

Once MRI scanner 111 has captured an image 206, image 206 has a further frame of reference 208. Frame of reference 208 can take a variety of forms, but generally includes an origin identified by its location within frame of reference 200, and axes indicating distances from that origin. Coordinates may be stored within image 206 (for example, in association with each pixel or voxel) according to the Digital Imaging and Communications in Medicine (DICOM) standard.

As will now be apparent to those skilled in the art, frame of reference 208 may be relatively easily transformed to frame of reference 200, but may be less amenable to transformation to frame of reference 204. Conventional mechanisms for determining which location on patient 104 (that is, within frame of reference 204) corresponds to a given location in image 206 (that is, within frame of reference 208) generally require manual intervention in which surgical instruments having fiducial markers mounted thereon are pointed at locations on patient 104 that correspond to predetermined locations in image 206. The positions and orientations of such instruments are determined by tracking system 112 in a frame of reference 212. Frame of reference 212 may have an origin at a known location within operating theatre 100 (that is, within the field of view of the camera of tracking system 112, illustrated in FIG. 2). Coordinates within frame of reference 212 thus define locations within operating theatre 100, independently of patient 104 and MRI scanner 111. Tracking system 112 can also determine the location of patient 104 in frame of reference 212 (by detection of marker 114), and thus the use of tracked surgical instruments to identify portions of patient 104 corresponding to predetermined points in image 206 allows image 206 to be registered to patient 104 in frame of reference 212.

As will be discussed below, the computing device in equipment tower 108 is configured to perform various actions that may facilitate the above-mentioned transformations among frames of reference 200, 204 and 208.

Figure 3:
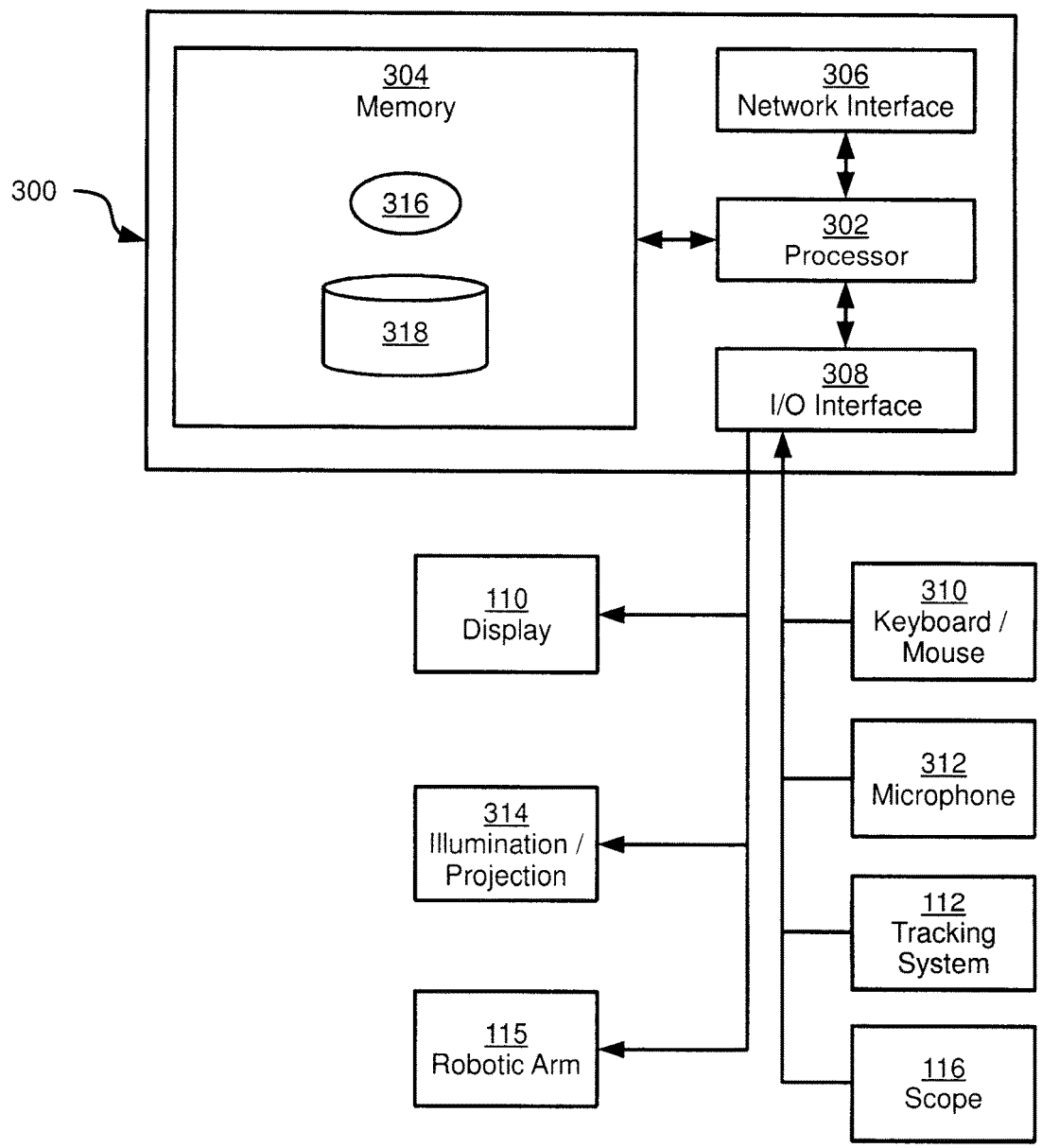
FIG. 3 depicts a computing device implemented in the operating theatre of FIG. 1, according to a non-limiting embodiment.

Before a discussion of the functionality of the computing device, a brief description of the components of the computing device will be provided. Referring to FIG. 3, a computing device 300 is depicted, including a central processing unit (also referred to as a microprocessor or simply a processor) 302 interconnected with a non-transitory computer readable storage medium such as a memory 304.

Processor 302 and memory 304 are generally comprised of one or more integrated circuits (ICs), and can have a variety of structures, as will now occur to those skilled in the art (for example, more than one CPU can be provided). Memory 304 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 304 includes both a volatile memory and a non-volatile memory. Other types of non-transitory computer readable storage medium are also contemplated, such as compact discs (CD-ROM, CD-RW) and digital video discs (DVD).

Computing device 300 also includes a network interface 306 interconnected with processor 300. Network interface 306 allows computing device 300 to communicate with other computing devices via a network (e.g. a local area network (LAN), a wide area network (WAN) or any suitable combination thereof). Network interface 306 thus includes any necessary hardware for communicating over such networks, such as radios, network interface controllers (NICs) and the like.

Computing device 300 also includes an input/output interface 308, including the necessary hardware for interconnecting processor 302 with various input and output devices. Interface 308 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 308, computing device 300 is connected to input devices including a keyboard and mouse 310, a microphone 312, as well as external scope 116 and tracking system 112, mentioned above. Also via interface 308, computing device 300 is connected to output devices including illumination or projection components 314 (e.g. lights, projectors and the like), as well as display 110 and robotic arm 115 mentioned above. Other input (e.g. touch screens) and output devices (e.g. speakers) will also occur to those skilled in the art.

It is contemplated that I/O interface 308 may be omitted entirely in some embodiments, or may be used to connect to only a subset of the devices mentioned above. The remaining devices, or all devices if I/O interface 308 is omitted, may be connected to computing device 300 via network interface 306.

Computing device 300 stores, in memory 304, an image registration application 316 (also referred to herein as application 316) comprising a plurality of computer readable instructions executable by processor 302. When processor 302 executes the instructions of application 316 (or, indeed, any other application stored in memory 304), processor 302 performs various functions implemented by those instructions, as will be discussed below. Processor 302, or computing device 300 more generally, is therefore said to be "configured" or "operating" to perform those functions via the execution of application 316.

Also stored in memory 304 are various data repositories, including a patient data repository 318. Patient data repository 318 can contain a surgical plan defining the various steps of the minimally invasive surgical procedure to be conducted on patient 104, as well as image data relating to patient 104, such as images captured using MRI scanner 111.

As mentioned above, computing device 300 is configured, via the execution of application 316 by processor 302, to perform various actions related to capturing images with MRI scanner 111 and registering such images to each other and to patient 104. Those functions will be described in further detail below.

Figure 4:
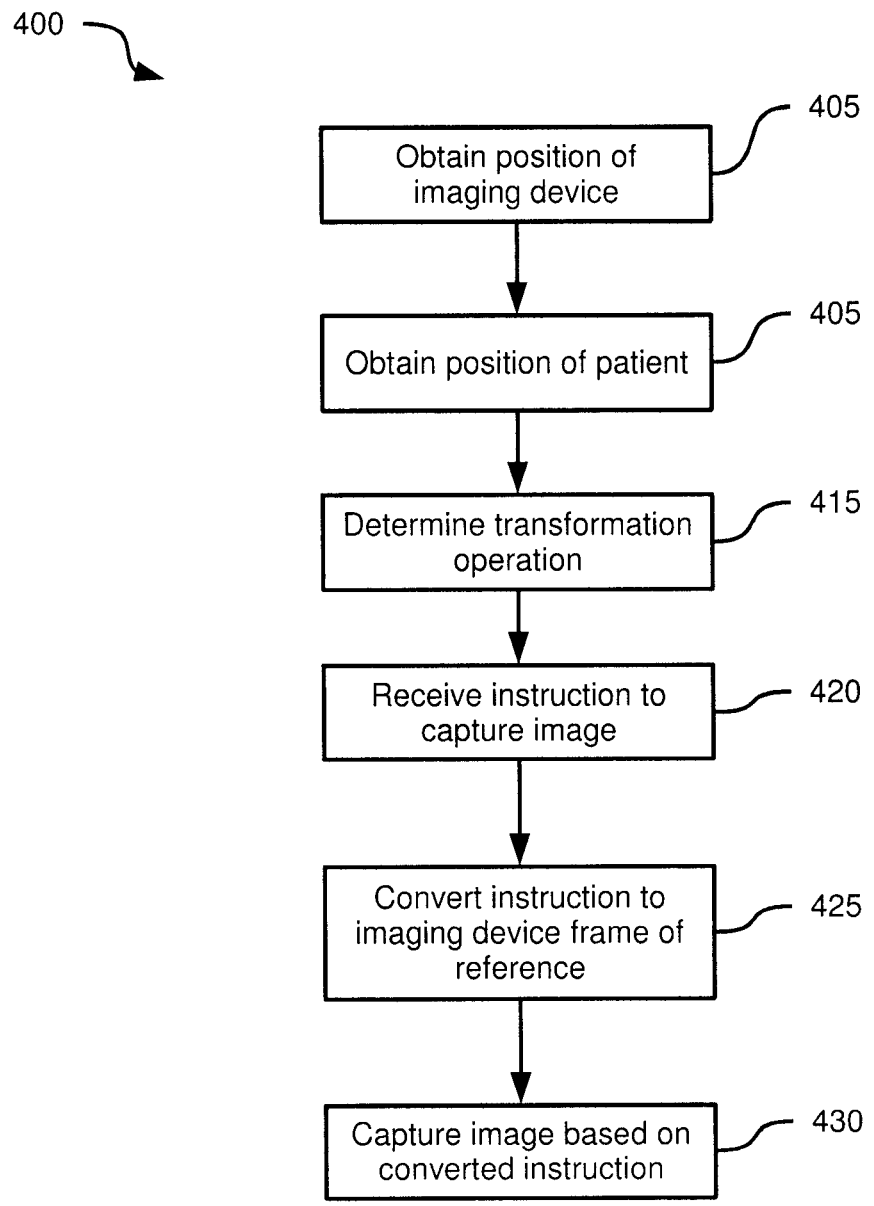
FIG. 4 depicts a method of capturing images with the MRI scanner in the operating theatre of FIG. 1, according to a non-limiting embodiment.

Referring now to FIG. 4, a method 400 of processing images is depicted. Method 400 will be discussed in conjunction with its performance on computing device 300 as deployed in operating theatre 100. It will be apparent to those skilled in the art, however, that method 400 can also be implemented on other computing devices in other systems.

Beginning at block 405, computing device 300 is configured to obtain the position of an imaging device such as MRI scanner 111. In particular, the position obtained at block 405 is obtained within frame of reference 212 (that is, the physical location of MRI scanner 111 within operating theatre 100). The position of MRI scanner 111 within operating theatre 100 may be obtained from tracking system 112. Tracking system 112, either independently or in conjunction with computing device 300, can be configured to detect marker 113 (and any other markers affixed to MRI scanner 111) and, based on the positions of such markers and a stored model of MRI scanner 111's geometry, determine the position and orientation of MRI scanner 111 within operating theatre 100.

At block 410, computing device 300 is configured to obtain the position of patient 104. As at block 405, the position obtained at block 410 is obtained within frame of reference 212 (that is, the location of patient 104 is obtained as coordinates within frame of reference 212). The position may be obtained by computing device 300 via receipt from tracking system 112, which detects marker 114 (and any other markers affixed to patient 104), or the position may be obtained by computing device 300 by assisting tracking system 112 in the determination of the position.

Figure 5:
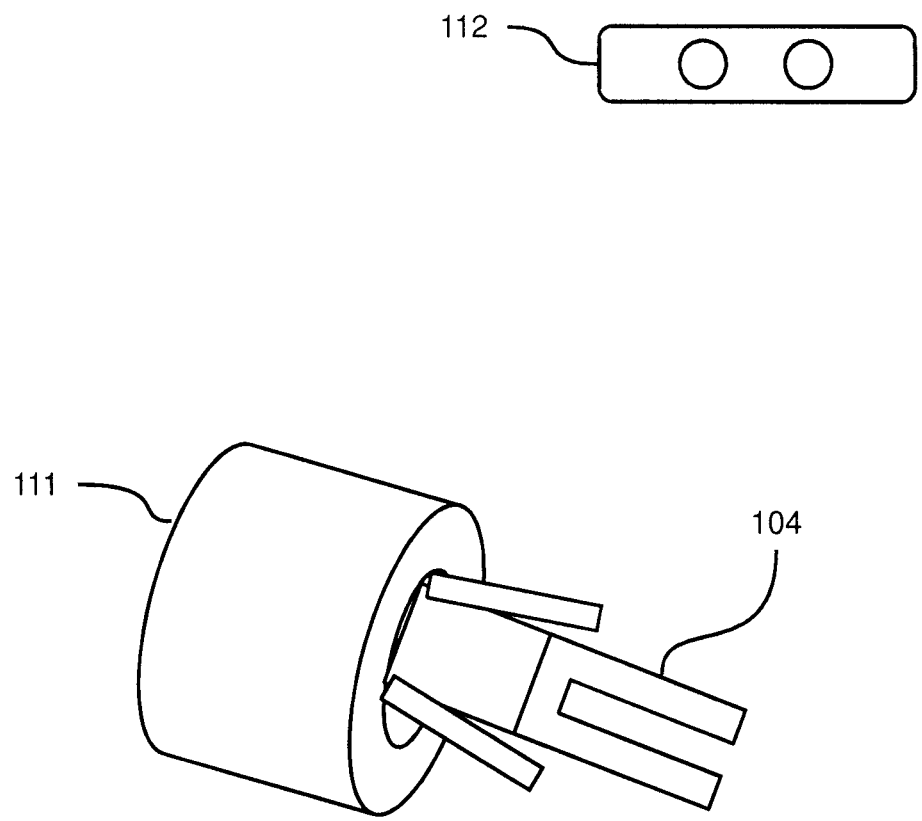
FIG. 5 depicts the patient and MRI scanner of the operating theatre of FIG. 1 arranged to capture images, according to a non-limiting embodiment.

Blocks 405 and 410 can be performed substantially simultaneously. That is, tracking system 112 may capture an image that encompasses both markers 113 and 114, and based on that image, determine both of the above-mentioned positions. In general, blocks 405 and 410 are performed when patient 104 is positioned within MRI scanner 111 prior to the capture of one or more images of patient 104, as illustrated in FIG. 5. It is contemplated that markers 113 and 114 may be located at any suitable position on MRI scanner 111 and patient 104, respectively, to ensure visibility of the markers to the camera of tracking system 112. In some embodiments, a marker may be placed on bed 105 instead of on MRI scanner 111. In such embodiments, bed 105 may be configured to enter into a fixed mechanical engagement with MRI scanner 111, such that detection of the marker on bed 105 allows tracking system 112 to accurately determine the position of MRI scanner 111.

Having obtained the positions of MRI scanner 111 and patient 104 in frame of reference 212, at block 415 computing device 300 is configured to determine a transformation operation for transforming coordinates in frame of reference 200 into coordinates in frame of reference 204, or vice versa. Such a transformation operation allows the coordinates identifying a given point in space to be converted to a different coordinate system, while still identifying the same point in space. The determination at block 415 is based on a comparison of the relative positions of MRI scanner 111 and patient 104 in frame of reference 212.

For example, computing device 300 may be configured to determine the distance between the known location on MRI scanner 111 representing the origin of frame of reference 200, and the known location on patient 104 representing the origin of frame of reference 204. Based on the distance between those origins, computing device 300 can determine the transformation operation. A variety of conventional algorithms may be used to determine the transformation operation, which may require one or more of translation, rotation, and scaling of coordinates in one frame of reference in order to identify the same point in space in another frame of reference.

The transformation operation at block 415 may be stored in memory 304, for example in repository 318. Following determination of the transformation operation, computing device 300 can be configured to receive an instruction to capture an image of patient 104. The instruction can be received in a variety of ways. For example, the instruction may be received via mouse and keyboard 310. In some embodiments, display 110 can present a model of patient 104, and based on knowledge of anatomical structures, an operator of computing device 300 (e.g. a medical professional) can select a location on the model corresponding to the desired target area of patient 104 for imaging. The selected location can be identified in the patient frame of reference 204.

At block 425, computing device 300 can be configured to convert the location identified in the instruction received at block 420 into the MRI scanner 111's frame of reference 200. The conversion at block 425 is achieved by applying the transformation operation determined at block 415 to the instruction received at block 420. As a result of applying the transformation operation, each coordinate in the instruction (which identifies a portion of patient 104) is converted into a coordinate in frame of reference 200 (while still identifying the same portion of patient 104).

Having converted the coordinates in the instruction, at block 430 computing device 300 is configured to cause MRI scanner 111 to capture one or more images based on the converted coordinates. As will be understood by those in the art, MRI scanner 111 is capable of receiving coordinates in frame of reference 200, which identify locations within MRI scanner 111, and capture images of those locations. Due to the transformation process described above, those locations contain the portions of patient 104 for which images are desired.

The image, or images, captured at block 430 can be stored in memory 304, for example in repository 318. As mentioned above, the images captured at block 430 contain coordinates (for example associated with each pixel or voxel of the images) in frame of reference 208, which has an origin at a known location within MRI scanner 111 (that is, within frame of reference 200). In some embodiments, the transformation determined at block 415 can be applied to the images captured at block 430, and the images can thus be stored in memory 304 with coordinates in frame of reference 204 associated with each pixel or voxel, rather than coordinates in frame of reference 208. In other embodiments, the captured images can be stored with the original coordinates (that is, those in frame of reference 208), and the transformation determined at block 415 can be stored in association with those images for later use.

It is contemplated that method 400 can be repeated any number of times, both preoperatively and intraoperatively, with each performance resulting in the storage of one or more images and a transformation operation associated with those images. As will be discussed below, computing device 300 can also be configured to perform additional actions related to the images captured via method 400.

Figure 6:
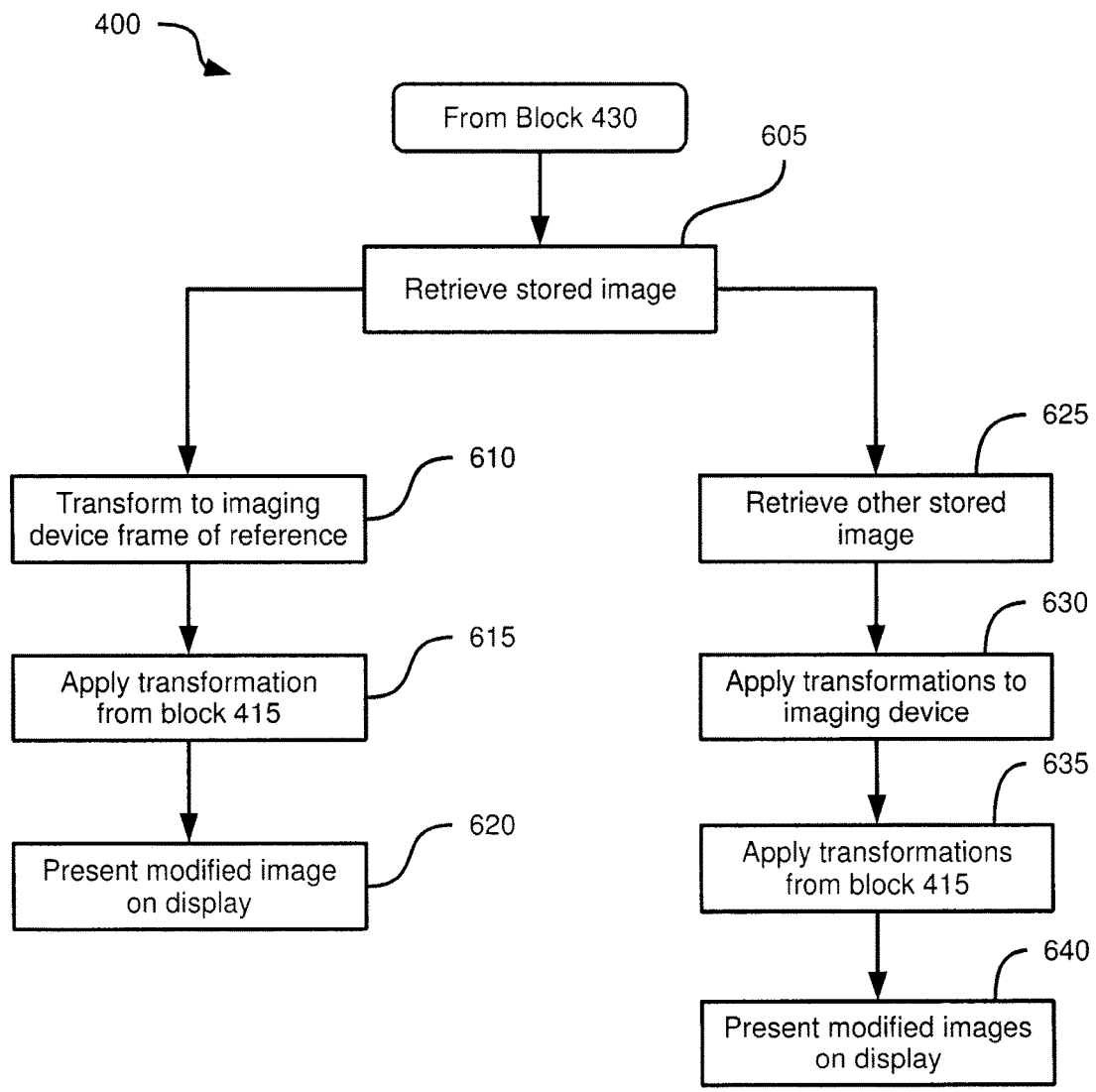
FIG. 6 depicts a method of registering images in the operating theatre of FIG. 1, according to a non-limiting embodiment.

Referring now to FIG. 6, a method 600 for image registration is illustrated. Method 600 will be discussed in conjunction with its performance on computing device 300 as deployed in operating theatre 100. It will be apparent to those skilled in the art, however, that method 600 can also be implemented on other computing devices in other systems.

Method 600 is assumed to take place after at least one performance of method 400. At block 605, computing device 300 is configured to retrieve an image captured at block 430, for example in response to an instruction received via keyboard and mouse 310. Following block 605, method 600 comprises two branches, which may be performed independently. The first branch permits computing device 300 to register the image retrieved at block 605 to patient 104 (that is, to frame of reference 204), and the second branch permits computing device 300 to register the image retrieved at block 605 with another image, acquired in a different performance of block 430.

The first branch mentioned above begins at block 610. At block 610, computing device 300 is configured to apply a transformation to the image retrieved at block 605 to convert the coordinates in the image (reference frame 208) to coordinates in frame of reference 200. Because the origin of frame of reference 208 is at a known location within frame of reference 200, the transformation applied at block 610 is based on the position of the origin of frame of reference 208 within frame of reference 200. For example, if the origin of frame of reference 208 is at the point (0, 10, 0) within frame of reference 200, then all points in the image can be converted to points in frame of reference 200 by applying the operation (0, +10, 0) to each point. More generally, the geometry of imaging device 111 is known, and there is a fixed, known transformation between reference frames 200 and 208. In some embodiments, the image retrieved at block 605 can even contain coordinates from reference frame 200 as metadata, and thus the transformation at block 610 includes simply retrieving those coordinates.

At block 615, computing device 300 is configured to apply the transformation determined at block 415 to the result of block 610. Thus, the image retrieved at block 605, which has been registered with the frame of reference of MRI scanner 111, is then registered with the frame of reference of patient 104. Following registration with patient 104, computing device 300 may be configured, for example, to present the image retrieved at block 605 on display 110 in conjunction with a model of patient 104. In some embodiments, further transformations may be applied in order to present the image on display 110 in conjunction with other tracked objects within operating theatre 100 (e.g. surgical instruments). Such transformations are based on the location of patient 104 within operating theatre 100 as detected by tracking system 112, and are known to those skilled in the art.

The second branch mentioned above begins at block 625, but need not be performed after the first branch. Indeed, the second branch may be performed before, after, instead of, or substantially simultaneously with, the first branch of method 600.

At block 625, computing device 300 can be configured to retrieve another image captured in a different performance of method 300. Thus, two images will be retrieved from memory 304, each image having a respective transformation operation determined at block 415.

At block 630, computing device 300 can be configured to apply transformations to each of the images retrieved at blocks 605 and 625 to convert the coordinates in those images to coordinates in frame of reference 200, as described in connection with block 610.

At block 635, computing device 300 can be configured to apply the respective transformations stored in association with each image, as determined at block 415. Thus, following the performance of block 635, the images retrieved at blocks 605 and 625 are registered with the patient frame of reference 204. As a result of the above registration, the images are therefore also registered with each other—that is, points in both images having the same coordinates depict the same portion of patient 104. Following such registration, the images can be presented simultaneously on display 110, for example as an overlay.

Various advantages to the above systems and methods will now be apparent to those skilled in the art. For example, the use of markers on MRI scanner 111 permits computing device 300 to identify the relative positions of MRI scanner 111 and patient 104, thus reducing or eliminating the need for manual procedures to align patient 104 within MRI scanner 111 prior to capturing images of patient 104. The process of method 400 may provide greater targeting accuracy during image capture because it provides for automatic targeting rather than manual alignment, and therefore it may be possible to omit the use of scout images during method 400.

As another example advantage, the storage of a transformation between MRI frame of reference 200 and patient frame of reference 204 in association with images captured with MRI scanner 111 may facilitate registration of the images both to each other and to patient 104. This may in turn reduce or eliminate the need to rely on manual registration techniques (e.g. pointing at various predetermined points with tracked instruments) to register images to patients, and may also reduce or eliminate the need to rely on error-prone image processing techniques such as edge detection to register images to each other.

Variations to the above systems and methods are contemplated. For example, rather than markers 113 and 114 as mentioned above, other tracking techniques may be employed, including surface scans of tracked objects (including MRI scanner 111 and patient 104) using structured light.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

We claim:
1. A method in a computing device, comprising:
at the computing device, obtaining a position of an imaging device in a tracking system frame of reference via a tracking system coupled to the computing device, the position of the imaging device comprising a first set of coordinates relative to an origin of the tracking system;
at the computing device, obtaining a position of a patient in the tracking system frame of reference via the tracking system, the position of the patient comprising a second set of coordinates relative to the tracking system origin;
determining, at the computing device, based on the position of the imaging device and the position of the patient, a transformation for registering an imaging device frame of reference defining a second origin with a patient frame of reference, wherein (i) the patient frame of reference is centered at a third origin located on the patient and distinct from the second set of coordinates, and (ii) defines a set of axes extending from the third origin, the axes aligned with anatomical planes of the patient;
receiving at the computing device, via an input device connected to the computing device, an instruction to capture an image, the instruction including a set of target coordinates identifying a target area of the patient according to the patient frame of reference;
generating a converted instruction from the instruction, by applying the transformation to convert the set of target coordinates to a fourth set of coordinates identifying the target area according to the imaging device frame of reference; and
capturing an image with the imaging device using the fourth set of coordinates in the converted instruction.

2. The method of claim 1, wherein the imaging device and the patient include markers, and wherein obtaining the positions of the imaging device and the patient comprises detecting the markers.

3. The method of claim 1, wherein obtaining the positions of the imaging device and the patient comprises receiving the positions from the tracking system.

4. The method of claim 1, wherein the imaging device is an MRI scanner.

5. The method of claim 1, further comprising:
storing the captured image in association with the transformation.

6. The method of claim 5, further comprising:
retrieving the stored image and the stored transformation;
applying the stored transformation to the image; and
presenting the transformed image on a display.

7. The method of claim 5, further comprising:
retrieving the stored image and the stored transformation;
retrieving a second image and a second corresponding transformation;
applying the respective transformations to the image and the second image; and
presenting the transformed image and the transformed second image on a display simultaneously.

8. A computing device, comprising:
an input device;
an interface;
a memory; and
a processor interconnected with the input device, the interface and the memory, the processor configured to:
obtain a position of an imaging device in a tracking system frame of reference via a tracking system coupled to the computing device, the position of the imaging device comprising a first set of coordinates relative to an origin of the tracking system;
obtain a position of a patient in the tracking system frame of reference via the tracking system, the position of the patient comprising a second set of coordinates relative to the tracking system origin;
determine, based on the position of the imaging device and the position of the patient, a transformation for registering an imaging device frame of reference defining a second origin with a patient frame of reference, wherein (i) the patient frame of reference is centered at a third origin located on the patient and distinct from the second set of coordinates, and (ii) defines a set of axes extending from the third origin, the axes aligned with anatomical planes of the patient;
receive, via the input device, an instruction to capture an image, the instruction including a set of target coordinates identifying a target area of the patient according to the patient frame of reference;
generate a converted instruction from the instruction, by applying the transformation to convert the set of target coordinates to a fourth set of coordinates identifying the target area according to the imaging device frame of reference; and
capture an image with the imaging device using the fourth set of coordinates in the converted instruction.

9. The computing device of claim 8, wherein the imaging device and the patient include markers; the processor configured to obtain the positions of the imaging device and the patient by detecting the markers.

10. The computing device of claim 8, the processor configured to wherein obtaining the positions of the imaging device and the patient comprises receiving the positions from the tracking system.

11. The computing device of claim 8, wherein the imaging device is an MRI scanner.

12. The computing device of claim 8, the processor further configured to:
store the captured image in the memory in association with the transformation.

13. The computing device of claim 12, further comprising a display connected to the processor; the processor further configured to:
retrieve the stored image and the stored transformation from the memory;
apply the stored transformation to the image; and
present the transformed image on the display.

14. The computing device of claim 12, further comprising a display connected to the processor; the processor further configured to:
retrieve the stored image and the stored transformation from the memory;
retrieve a second image and a second corresponding transformation from the memory;
apply the respective transformations to the image and the second image; and
present the transformed image and the transformed second image on the display simultaneously.

15. A non-transitory computer readable storage medium storing a plurality of computer-readable instructions executable by a processor of a computing device for performing a method comprising:
at the computing device, obtaining a position of an imaging device in a tracking system frame of reference via a tracking system coupled to the computing device, the position of the imaging device comprising a first set of coordinates relative to an origin of the tracking system;
at the computing device, obtaining a position of a patient in the tracking system frame of reference via the tracking system, the position of the patient comprising a second set of coordinates relative to the tracking system origin;

determining, at the computing device, based on the position of the imaging device and the position of the patient, a transformation for registering an imaging device frame of reference defining a second origin with a patient frame of reference, wherein (i) the patient frame of reference is centered at a third origin located on the patient and distinct from the second set of coordinates, and (ii) defines a set of axes extending from the third origin, the axes aligned with anatomical planes of the patient;

receiving at the computing device, via an input device connected to the computing device, an instruction to capture an image, the instruction including a set of target coordinates identifying a target area of the patient according to the patient frame of reference;

generating a converted instruction from the instruction, by applying the transformation to convert the set of target coordinates to a fourth set of coordinates identifying the target area according to the imaging device frame of reference; and capturing an image with the imaging device using the fourth set of coordinates in the converted instruction.

16. The non-transitory computer readable storage medium of claim 15, wherein the imaging device and the patient include markers, and wherein obtaining the positions of the imaging device and the patient comprises detecting the markers.

17. The non-transitory computer readable storage medium of claim 15, wherein obtaining the positions of the imaging device and the patient comprises receiving the positions from the tracking system.

18. The non-transitory computer readable storage medium of claim 15, wherein the imaging device is an MRI scanner.

19. The non-transitory computer readable storage medium of claim 15, the method further comprising:
   storing the captured image in association with the transformation.

20. The non-transitory computer readable storage medium of claim 19, the method further comprising:
   retrieving the stored image and the stored transformation;
   applying the stored transformation to the image; and
   presenting the transformed image on a display.

21. The non-transitory computer readable storage medium of claim 19, the method further comprising:
   retrieving the stored image and the stored transformation;
   retrieving a second image and a second corresponding transformation;
   applying the respective transformations to the image and the second image; and
   presenting the transformed image and the transformed second image on a display simultaneously.

* * * * *